United States Patent [19]

Beylin et al.

[11] Patent Number: 5,198,548

[45] Date of Patent: Mar. 30, 1993

[54] PROCESS FOR THE PREPARATION OF D(−) AND L(+)-3,3-DIPHENYLALANINE AND D(−) AND L(+)-SUBSTITUTED 3,3-DIPHENYLALANINES AND DERIVATIVES THEREOF

[75] Inventors: Vladimir Beylin; Huai G. Chen; Om P. Goel; John G. Topliss, all of Ann Arbor, Mich.

[73] Assignee: Warner-Lambert Company, Morris Plains, N.J.

[21] Appl. No.: 828,399

[22] Filed: Jan. 30, 1992

[51] Int. Cl.$^5$ .................... C07D 453/02; C07B 57/00; C07C 271/32; C07C 271/54
[52] U.S. Cl. .................................... 546/136; 546/134; 560/27; 560/38; 560/40; 562/401; 562/441
[58] Field of Search ............... 546/136, 134; 562/401, 562/441; 560/38, 40, 27

[56] References Cited

U.S. PATENT DOCUMENTS 4,603,145 7/1986 DeVries et al. ............... 562/441 X
4,988,730 1/1991 Korbonits et al. ............. 562/441 X

OTHER PUBLICATIONS

Tetrahedron Letters, vol. 32, No. 45, pp. 6547–6550, (1991).

*Primary Examiner*—José G. Dees
*Assistant Examiner*—Vera C. Clarke
*Attorney, Agent, or Firm*—Francis J. Tinney

[57] ABSTRACT

A process for the preparation of D(−) and L(+)-3,3-diphenylalanine and D(−) and L(+)-substituted 3,3-diphenylalanines is described where N-protected DL-3,3-diphenylalanine or N-protected-DL-substituted 3,3-diphenylalanine are treated with (−)cinchonidine and the resulting salt resolved into the desired enantiomers, as well as derivatives thereof and valuable intermediates used in the process.

12 Claims, No Drawings

PROCESS FOR THE PREPARATION OF D(−) AND L(+)-3,3-DIPHENYLALANINE AND D(−) AND L(+)-SUBSTITUTED 3,3-DIPHENYLALANINES AND DERIVATIVES THEREOF

BACKGROUND OF THE INVENTION

The present invention relates to a process for the preparation of D(−) and L(+) enantiomers of 3,3-diphenylalanine and D(−) and L(+) substituted 3,3-diphenylalanines and derivatives thereof which are used to prepare biologically active peptides useful as pharmaceutical agents.

The development of peptides as therapeutic agents has been hindered by the short duration of action and lack of oral activity of this class of compounds. Thus, unnatural amino acids have been used to replace natural amino acids in order to prepare analogs with enhanced potency and metabolic stability. In some cases these analogs were orally active.

Yabe, Y., et. al., *Chemical Pharmaceutical Bulletin*, Volume 24, pages 3149-3157 (1976) disclosed a series of Luteinizing Hormone-Releasing Hormone analogs containing various hydrophobic unnatural amino acid replacements at the 3-position with potent biological activity. Nestor, Jr., J. J., et. al., *Journal of Medicinal Chemistry*, Volume 25, pages 795-801 (1982) disclosed a series of Luteinizing Hormone-Releasing Hormone analogs containing various hydrophobic unnatural amino acid replacements at the 6-position with potent biological activity.

U.S. Pat. No. 4,766,109 disclosed a series of hydrophobic peptides having antihypertensive activity. In some cases the peptides contained racemic 3,3-diphenylalanine as the unnatural hydrophobic amino acid.

Hsieh, K-H, et. al., *Journal of Medicinal Chemistry*, 32:898-903 (1989) disclosed a series of angiotensin II analogs in which the phenylalanine at the 8-position was replaced with various unnatural amino acids including racemic 3,3-diphenylalanine. The authors used racemic 3,3-diphenylalanine since they were unable to resolve this amino acid using hog kidney acylase and carboxypeptidase. The octapeptide diastereomeric mixture containing racemic 3,3-diphenylalanine was subsequently separated by countercurrent distribution into the L- and D-diastereomeric peptides. The authors reported that the peptide diastereomer containing L-3,3-diphenylalanine in place of L-phenylalanine at the 8-position produced a twofold increase in activity.

Recently, Josien, H., et. al., Tetrahedron Letters 32 6447-6550 (1991) disclosed an asymmetric synthesis of L-(+)-3,3-diphenylalanine from a sultam derived glycine imine. However, this asymmetric synthesis requires long reaction times and proceeds in only 46% overall yield and 95% diastereomeric excess.

Therefore, there is a need to resolve racemic 3,3-diphenylalanine and various substituted derivatives thereof into the L- and D-enantiomers for use in preparing various biologically active peptide analogs. We have surprisingly and unexpectedly found, contrary to previous literature disclosures that DL-3,3-diphenylalanine and various phenyl substituted derivatives can be resolved into the D(−) and L(+) enantiomers using (−)cinchonidine.

The object of the present invention is an efficient and economical process which is amenable to large-scale synthesis for the preparation of D(−) and L(+) 3,3-diphenylalanine and various phenyl substituted derivatives thereof which may be subsequently incorporated into biologically active peptides to prepare analogs with increased potency and/or metabolic stability.

SUMMARY OF THE INVENTION

Accordingly, a first aspect of the present invention is a process for the preparation of the D(−) and L(+) enantiomers of a compound of Formula I

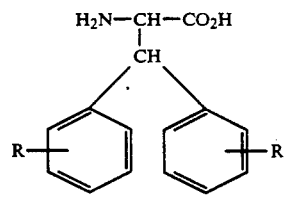

and pharmaceutically acceptable salts thereof wherein
R is hydrogen, chloro, bromo, fluoro, methyl, trifluoromethyl, methoxy, 2,4-dichloro, or 2,4-difluoro
which comprises:
Step (a) treating a racemic compound of Formula II

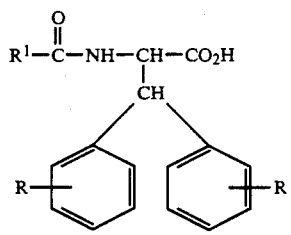

wherein
$R^1$ is lower alkyl,
$CX_3$ wherein X is hydrogen or halogen or aryl and
R is as defined above;
with (−)cinchonidine in a solvent to afford a racemic compound of Formula III;

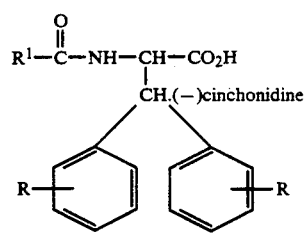

wherein R and $R^1$ are as defined above;
Step (b) resolving a compound of Formula III wherein R and $R^1$ are as defined above by fractional crystallization into D(−) and L(+) enantiomers:

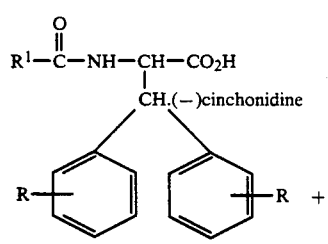

D(−)IIIa

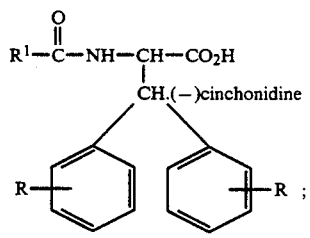

L(+)IIIb

Step (c) treating a compound of Formula D(−)IIIa or Formula L(+)IIIb wherein R and R¹ are as defined above with an acid in a solvent to afford a compound of Formula D(−)IIa or Formula L(+)IIb:

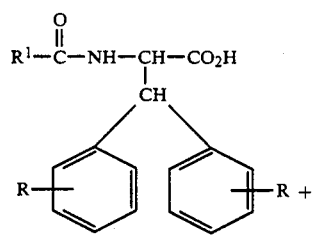

D(−)IIa

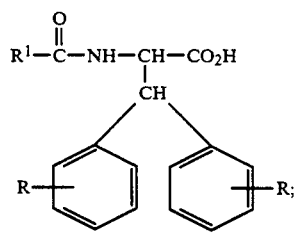

L(+)IIb

Step (d) heating a compound of Formula D(−)IIa or Formula L(+)IIb wherein R and R¹ are as defined above with an acid to afford the D(−)Ia or L(+)Ib enantiomers of Formula I;

Step (e) and, if desired, converting a compound of Formula D(−)Ia or Formula L(+)Ib to a corresponding pharmaceutically acceptable salt by conventional means, and if so desired, converting the corresponding pharmaceutically acceptable salt to a compound of Formula D(−)Ia or Formula L(+)Ib by conventional means.

A second aspect of the present invention is a novel intermediate selected from the group consisting of

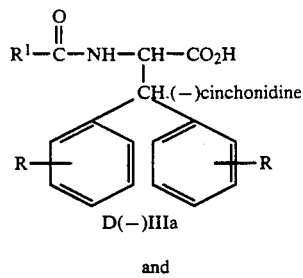

D(−)IIIa and

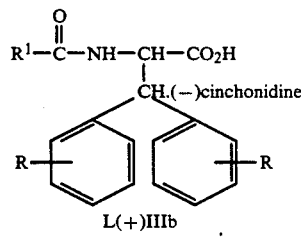

L(+)IIIb wherein R and R¹ are as defined above.

A third aspect of the present invention is a novel intermediate selected from the group consisting of

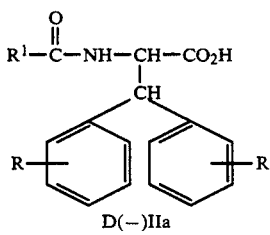

D(−)IIa and

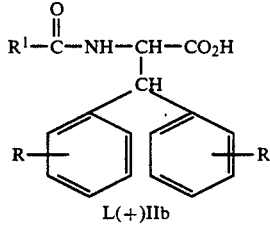

L(+)IIb wherein R and R¹ are as defined above and pharmaceutically acceptable salts thereof.

A fourth aspect of the present invention is a novel compound of Formula D(−)Ia

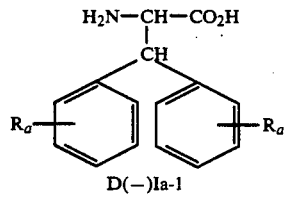

D(−)Ia-1 wherein
  $R_a$ is chloro, bromo, fluoro, methyl, trifluoromethyl, methoxy, 2,4-dichloro, or 2,4-difluoro
and pharmaceutically acceptable salts thereof.

A fifth aspect of the present invention is a novel compound of Formula L(+)Ib

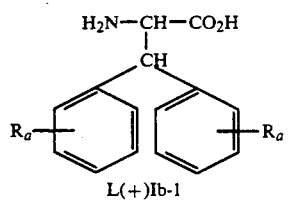

L(+)Ib-1 wherein $R_a$ is chloro, bromo, fluoro, methyl, trifluoromethyl, methoxy, 2,4-dichloro, or 2,4-difluoro and pharmaceutically acceptable salts thereof.

A sixth aspect of the present invention is the novel compound of Formula D(−)IVa

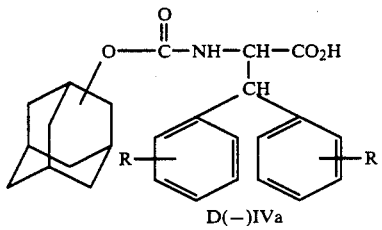

D(−)IVa wherein R is as defined above and pharmaceutically acceptable salts thereof.

A seventh aspect of the present invention is the novel compound of Formula L(+)IVb

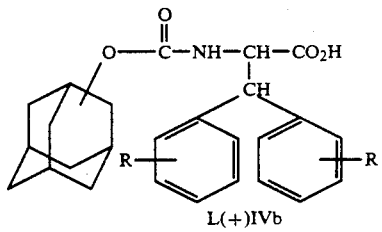

L(+)IVb wherein R is as defined above and pharmaceutically acceptable salts thereof.

An eighth aspect of the present invention is the novel compound of Formula D(−)Va

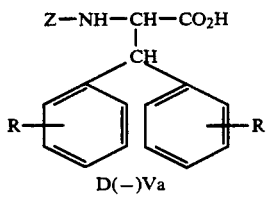

D(−)Va wherein Z is benzyloxycarbonyl and R is as defined above and pharmaceutically acceptable salts thereof.

A ninth aspect of the present invention is the novel compound of formula L(+)Vb

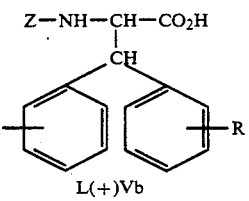

L(+)Vb wherein Z is benzyloxycarbonyl and R is as defined above and pharmaceutically acceptable salts thereof.

DETAILED DESCRIPTION OF THE INVENTION

In this invention, the term "lower alkyl" means a straight or branched hydrocarbon radical having from one to six carbon atoms and includes, for example, methyl, ethyl, n-propyl, isopropyl, n-butyl, sec-butyl, isobutyl, tert-butyl, n-pentyl, n-hexyl, and the like.

The term "aryl" means an aromatic radical which is a phenyl group or phenyl group substituted by one to two substituents selected from lower alkyl, halogen, or nitro.

"Halogen" is fluorine, chlorine, bromine, or iodine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

The following table provides a list of abbreviations and definitions thereof used in the present invention.

| Abbreviation* | |
|---|---|
| | Amino Acid |
| Asp | Aspartic Acid |
| Dip | 3,3-Diphenylalanine |
| Ile | Isoleucine |
| Leu | Leucine |
| Trp | Tryptophan |
| | Protecting Group |
| Ac | Acetyl |
| Bzl | Benzyl |
| Boc | tertiary-Butyloxycarbonyl |
| For | Formyl |
| Z | Benzyloxycarbonyl |
| | Solvents and Reagents |
| HOAc | Acetic Acid |
| CH₃CN | Acetonitrile |
| DCM | Dichloromethane |
| DCC | N,N'-Dicyclohexyl-carbodiimide |
| DIEA | N,N'-Diisopropylethylamine |
| DMF | Dimethylformamide |
| HCl | Hydrochloric acid |
| KOH | Potassium hydroxide |
| NaOH | Sodium hydroxide |
| KHMDS | Potassium bis(trimethylsilyl)amide |
| TFA | Trifluoroacetic acid |
| PAM Resin | 4-(Oxymethyl)-phenylacetamidomethyl resin |

*If the optical activity of the amino acid is other than L (S), the amino acid or abbreviation is preceded by the appropriate configuration D (R) or DL (RS).

The compounds of Formula D(−)Ia and Formula L(+)Ib are capable of forming both pharmaceutically acceptable acid addition and/or base salts. The compounds of Formulas D(−)IIa, L(+)IIb, D(−)IVa, L(+)IVb, D(−)Va, and L(+)Vb are capable of forming pharmaceutically acceptable base addition salts. All of these forms are within the scope of the present invention.

Pharmaceutically acceptable acid addition salts of a compound of Formula D(−)Ia and Formula L(+)Ib include salts derived from nontoxic inorganic acids such as hydrochloric, nitric, phosphoric, sulfuric, hydrobromic, hydriodic, phosphorous and the like, as well as the salts derived from nontoxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebecate, fumarate, maleate, mandelate, benzoate, chlorobenzoate, methylbenzoate, nitrobenzoate, phthalate, benzenesulfonate, toluenesulfonate, phenylacetate, citrate, lactate, maleate, tartrate, methanesulfonate and the like. Also contemplated are salts of amino acids such as arginate and the like and gluconate, galacturonate (see, for example, Berge, S. M., et. al., "Pharmaceutical Salts," *Journal of Pharmaceutical Science*, 66:1–19 (1977).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Pharmaceutically acceptable base addition salts are formed with metals or amines such as alkali and alkaline earth metals or organic amines. Examples of metals used as cations are sodium, potassium, magnesium, calcium and the like. Examples of suitable amines are N,N'-dibenzylethylenediamine, chloroprocaine, choline, diethanolamine, ethylenediamine, N-methylglucamine, and procaine (see, for example, Berge, S. M., et. al., *Journal of Pharmaceutical Science*, 66:1–19 (1977)).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acids for purposes of the present invention.

A compound of Formulas Ia, IIa, IVa, or Va may be designated either as D(−) or R(−) and a compound of Formulas Ib, IIb, IVb, or Vb as L(+) or S(+), respectively.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

As previously described, the compounds of Formula D(−)Ia and Formula L(+)Ib, are useful as hydrophobic unnatural amino acid replacements to prepare biologically active peptides with enhanced potency and/or metabolic stability.

The process of the present invention in its first aspect is a new, economical, and commercially feasible method for resolving racemic 3,3-diphenylalanine and substituted phenyl derivatives thereof into the D(−) and L(+) enantiomers. The process of the present invention in its first aspect is outlined in Scheme I.

SCHEME I

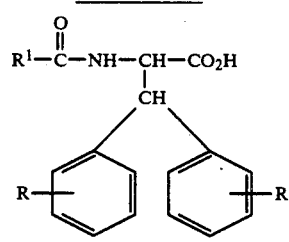

-continued
SCHEME I
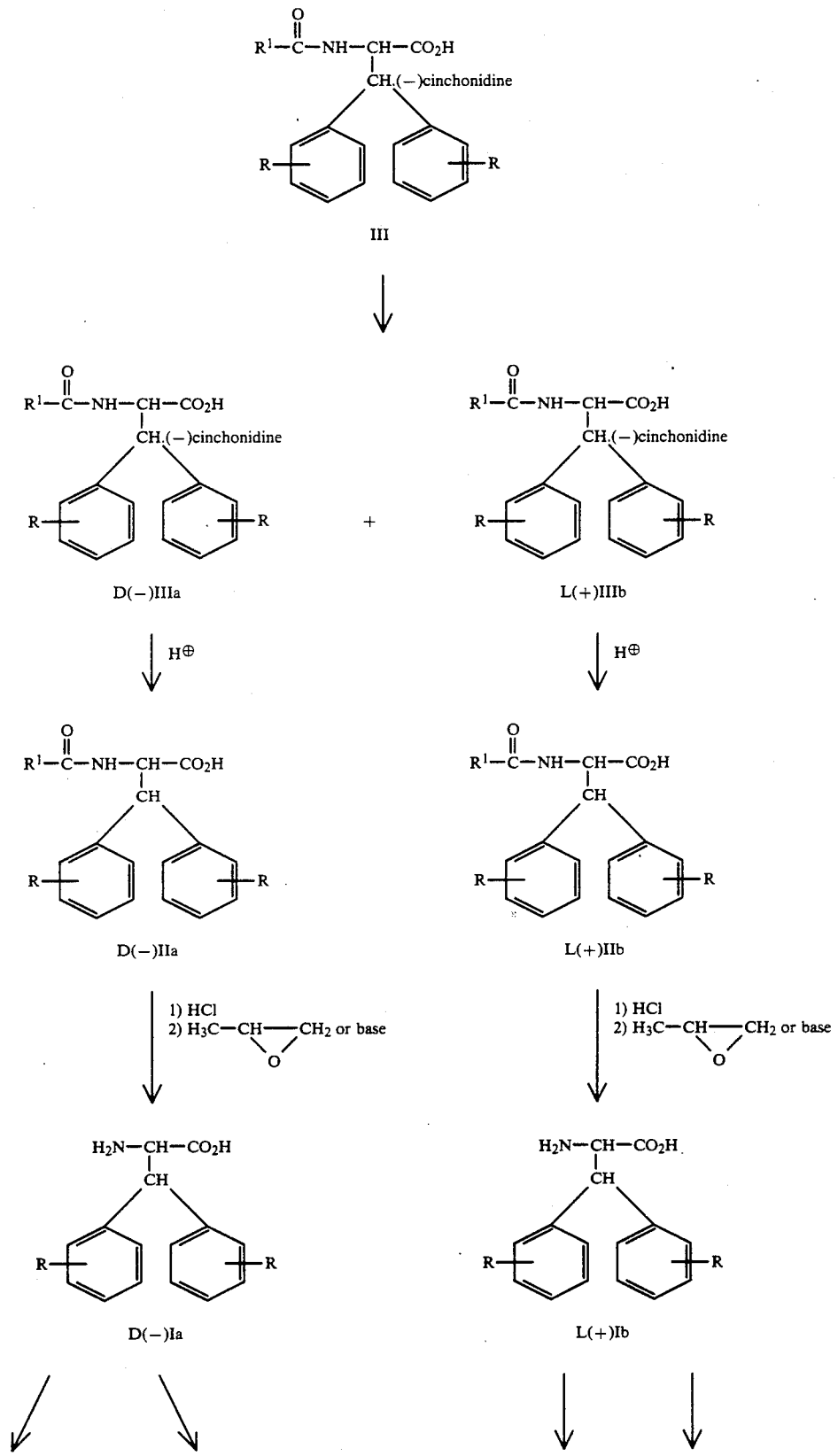

-continued
SCHEME I

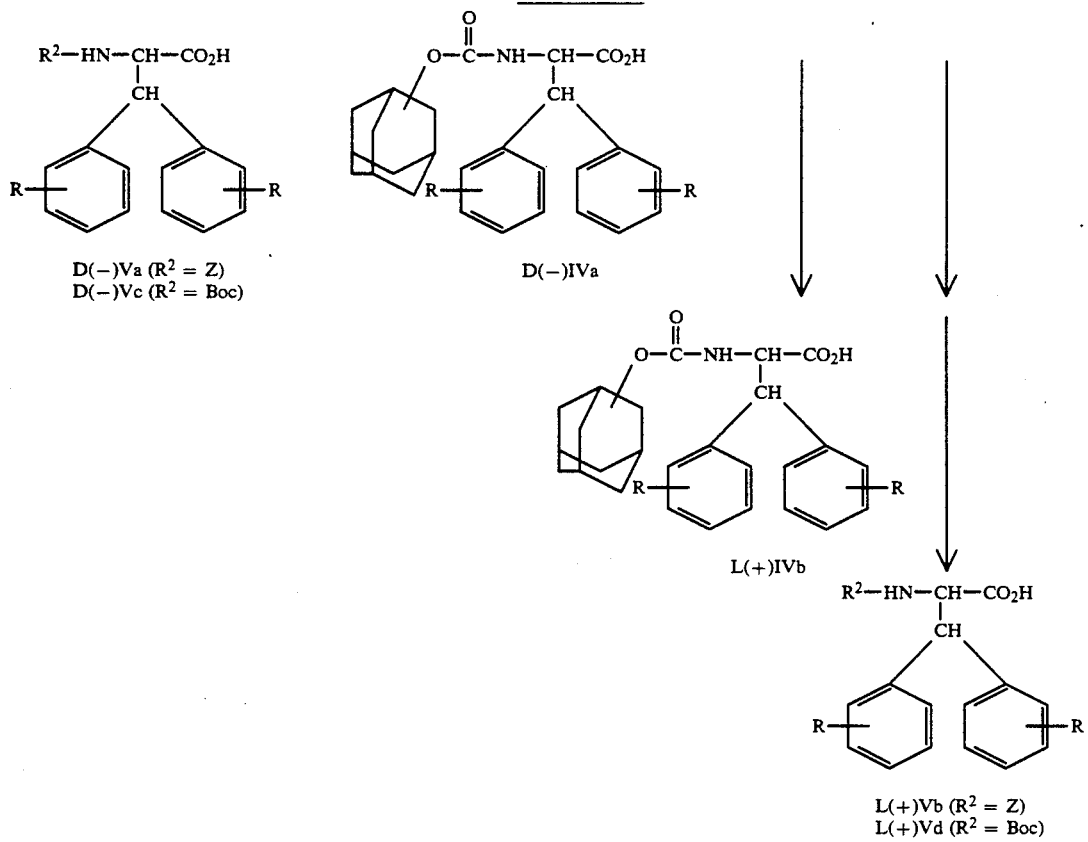

Thus, a compound of Formula II which is a racemic mixture of isomers is treated with (—)-cinchonidine in a solvent such as, for example, an alcohol, for example, methanol, ethanol, propanol, butanol, and the like, preferably methanol, at about 10° C. to about 100° C. to afford a (—)cinchonidine salt of Formula III. A solution of a compound of Formula III is cooled to about —20° C. to about 25° C. to afford by fractional crystallization a compound of Formula D(—)IIIa and a compound of Formula L(+)IIIb. Preferably, the reaction is carried out by refluxing the compound of Formula II with (—)cinchonidine in methanol and cooling to about 2° C. to separate the enantiomers by fractional crystallization. A compound of Formula D(—)IIIa or Formula L(+)IIIb is treated with an acid such as, for example, hydrochloric acid and the like in a solvent such as, for example, ethyl acetate, dichloromethane, chloroform, toluene, tetrahydrofuran, diethyl ether, and the like at about 0° C. to about 60° C. to afford a compound of Formula D(—)IIa or Formula L(+)IIb. Preferably, the reaction is carried out with hydrochloric acid in ethyl acetate at about room temperature. A compound of Formula D(—)IIa or Formula L(+)IIb is heated with an acid such as, for example, hydrochloric acid, sulfuric acid, para toluenesulfonic acid, and the like to afford a compound of Formula D(—)Ia or Formula L(+)Ib as an acid addition salt. Preferably, the reaction is carried out by refluxing in hydrochloric acid.

The acid addition salt of a compound of Formula D(—)Ia or Formula L(+)Ib is treated with a base such as, for example, ammonium hydroxide, to afford a compound of Formula D(—)Ia or Formula L(+)Ib, respectively, as the free amino acid. Alternatively, the acid addition salt of a compound of Formula D(—)Ia or Formula L(+)Ib may be treated with propylene oxide using the methodology of Schollkopf, U., et. al., *Synthesis*, pp. 966 969 (1981) to afford a compound of Formula D(—)Ia or Formula L(+)Ib, respectively, as the free amino acid. A compound of Formula D(—)Ia or Formula L(+)Ib is treated with 1- or 2-adamantyl chloroformate or fluoroformate in the presence of a base such as, for example, sodium hydroxide and the like in a solvent such as, for example, water-tetrahydrofuran and the like at about 0° C. to about room temperature to afford, respectively, a compound of Formula D(—)IVa or Formula L(+)IVb wherein the oxygen atom of the carbamate is attached at the 1-or 2 position of the adamantane ring. Preferably, the reaction is carried out in the presence of sodium hydroxide in water-tetrahydrofuran at about 0° C.

Additionally, a compound of Formula D(—)Ia or Formula L(+)Ib is treated with benzylchloroformate using the methodology used to prepare a compound of Formula D(—)IVa or Formula L(+)IVb from a compound of Formula D(—)Ia or Formula L(+)Ib to afford a compound of Formula D(—)Va or Formula L(+)Vb.

The N-α-tertiary-butyloxycarbonyl (Boc) derivatives (Formulas D( )Vc and L(+)Vd) of a compound of Formula D(—)Ia or Formula L(+)Ib are prepared from a compound of Formula D( )Ia or Formula L(+)Ib according to the methodology used to prepare Boc DL-3,3-diphenylalanine disclosed in U.S. Pat. No. 4,766,109. The Boc derivatives may also be prepared by other conventional methodology known in the art.

The absolute configuration of the D- and L-enantiomers of a compound of Formula Ia and Formula Ib are assigned based on the order of elution using Diacel Crownpack High Pressure Liquid Chromatography columns according to methodology disclosed by Shinbo, T., et. al., *Journal of Chromatography*, 405:145-153 (1987) and Hilton, M. and Armstrong, D. W., *Journal of Liquid Chromatography*, 14:9-28 (1991).

The configuration of a compound of Formula Ia or Formula Ib is confirmed by a chiral synthesis of D-and L-Dip using methodology disclosed by Evans, D. A., et. al., *Journal of the American Chemical Society* 112:4011-4030 (1990) and Evans, D. A., et. al., *Journal of the American Chemical Society* 111:1063-1072 (1989) as outlined in Scheme II and Scheme III.

Thus, as outlined in Scheme II, 3,3-diphenylpropionic acid (XIV) is treated with thionyl chloride in the presence of pyridine to afford the acid chloride (XIII).

Sodium azide is added to a solution of 2,4,6-triisopropylbenzenesulfonyl chloride (XII) in a solvent such as, for example, ethanol and the like to afford the azide (XI). (1S,2R)-Norephedrine (X) is treated with diethyl carbonate in the presence of a base such as, for example, potassium carbonate, to afford (4R,5S)-4-methyl-5-phenyl-2-oxazolidinone (IX). A solution of the acid chloride (XIII) in a solvent such as, for example, tetrahydrofuran and the like, is added to the lithiated oxazolidinone solution in a solvent such as, for example, tetrahydrofuran and the like (the lithiated oxazolidinone is prepared by treating a compound of Formula IX with n-butyl lithium) to afford the acyloxazolidinone (VIII). Deprotonation of VIII by treating with potassium bis(trimethylsilyl)amide (KHMDS) in a solvent such as, for example, tetrahydrofuran and the like, followed by the addition of a solution of the azide (XI) in a solvent such as, for example, tetrahydrofuran and the like and rapid quenching with an acid such as, for example, acetic acid and the like to afford the azido oxazolidinone (VII). The azido oxazolidinone (VII) is hydrolyzed with lithium hydroxide in hydrogen peroxide to afford the azido acid (VI). Treatment of the azido acid (VI) with hydrogen in the presence of a catalyst such as, for example, palladium on carbon and the like, in acetic acid followed by azeotropic evaporation with heptane after uptake of hydrogen and subsequent addition of hydrochloric acid affords (2R)-3,3-diphenylalanine hydrochloride (Ic).

(2S)-3,3-Diphenylalanine hydrochloride (Id) is prepared using the same methodology as used to prepare (2R)-3,3-diphenylalanine (Ic) by substituting (4S,5R)-4-methyl-5-phenyl-2-oxazolidinone (IXa) for (4R,5S)-4-methyl-5-phenyl-2-oxazolidinone (IX) as outlined in Scheme III.

SCHEME II

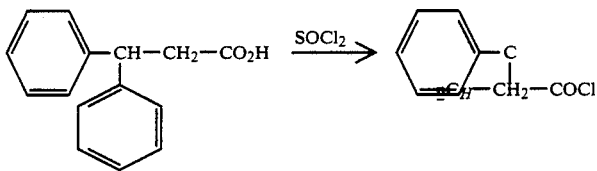

XIV

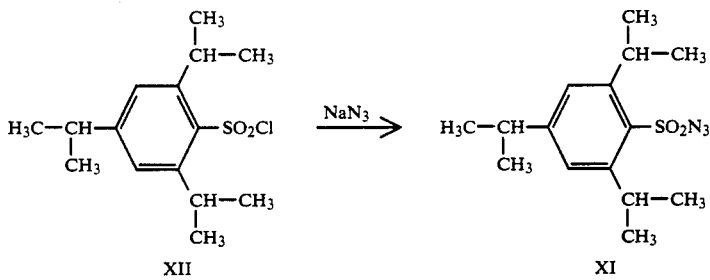

XII     XI

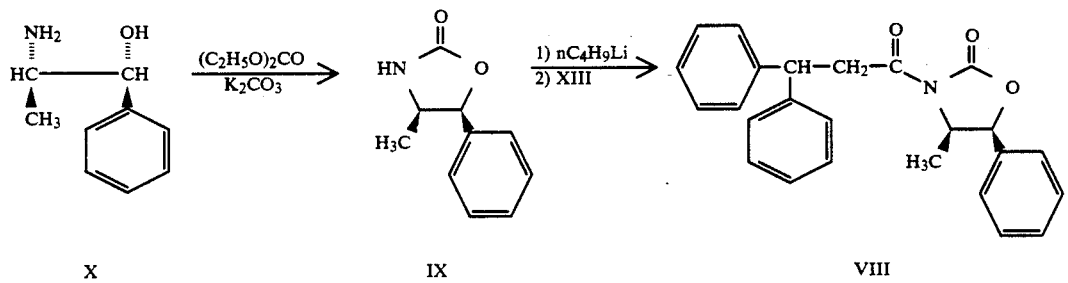

X       IX      VIII

1) KHMDS, −78° C.
2) XI

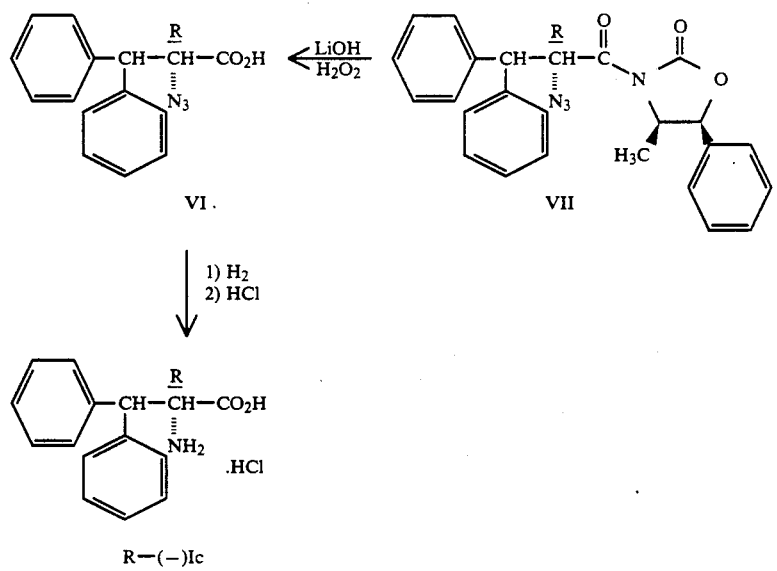
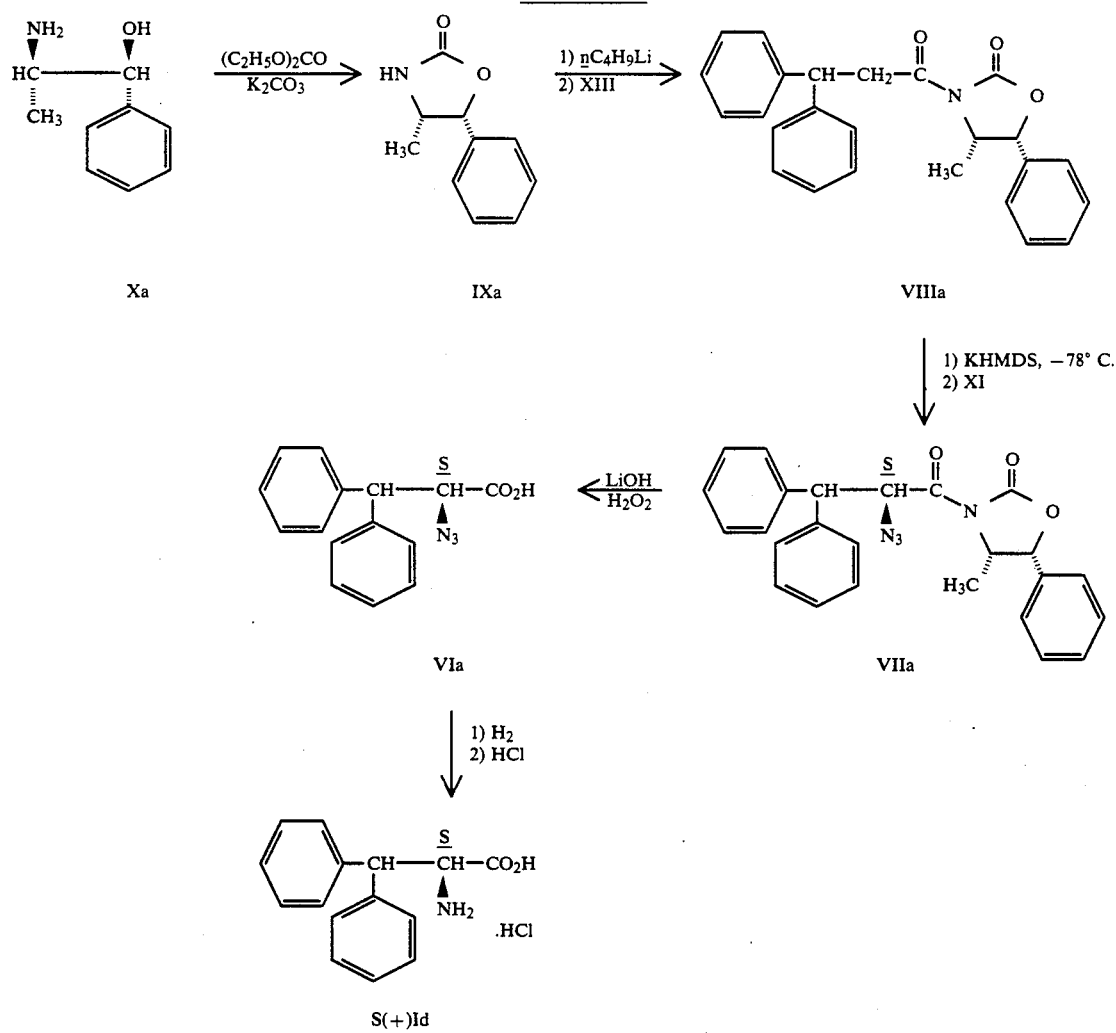

A racemic compound of Formula II is prepared by treating the racemic compound of Formula I with a compound of

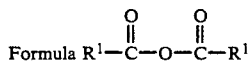

Formula $R^1—C(=O)—O—C(=O)—R^1$ wherein $R^1$ is as defined above in the presence of a base such as, for example, an alkali metal hydroxide or alkaline earth metal hydroxide or carbonate, for example, sodium hydroxide and the like to afford a compound of Formula II.

A racemic compound of Formula I is prepared from benzophenone imine or a substituted benzophenone imine using the methodology described by O'Donnell, M. J. and Eckrich, T. M., *Tetrahedron Letters*, pages 4625-4628 (1978); O'Donnell, M. J. and Polt, R. L., *Journal of Organic Chemistry* 47:2663-2666 (1982); and O'Donnell, M. J., et. al., *Journal of the American Chemical Society* 111:2353-2355 (1989).

The following nonlimiting examples are illustrative to show the present process, the preparation of starting materials, and the use of D(−)-3,3-diphenylalanine obtained by the present process to prepare Acetyl-D-Dip-Leu-Asp-Ile-Ile-Trp, an antagonist of endothelin useful in the treatment of hypertension, myocardial infarction, metabolic, endocrinological and neurological disorders, congestive heart failure, endotoxic shock, subarachnoid hemorrhage, arrhythmias, asthma, acute renal failure, preeclampsia, and diabetes which is disclosed in copending U.S. Pat. No. application Ser. No. 07/809,746, filed Dec. 18, 1991.

EXAMPLE 1

D-(−)-3,3-Diphenylalanine

Step A: Preparation of N-Acetyl-D(−)-3,3-diphenylalanine cinchonidinium salt

To a hot solution of 62.0 g (0.211 mol) of (−)cinchonidine in 400 mL of methanol is added a hot solution of N-acetyl-DL-3,3-diphenylalanine (Example B) in 250 mL of methanol. The mixture is heated at reflux on a steam bath, and then cooled to room temperature. Some seed crystals from a previous experiment are added. After 1 hour at room temperature the mixture is placed in a refrigerator (+2° C.) overnight. The product is collected by filtration and dried in a vacuum oven at 55° C./200 mm Hg overnight to afford 36.5 g of a white crystalline product; mp 193°-195° C., $[\alpha]_D^{25} = -92°$ (1% in methanol).

The mother liquor is evaporated to dryness to afford 84.6 g of a white foam. This is recrystallized from 350 mL of methanol as described above to afford 3.6 g of product; mp192°-194° C., $[\alpha]_D^{25} = -84°$. The mother liquor is evaporated to afford 79.6 g of a solid; $[\alpha]_D^{25} -62°$ which is used in the preparation of L-(+)-enantiomer (see Example 2).

Step B: Preparation of N-Acetyl-D-(−)-3,3-diphenylalanine

N-Acetyl-D(−)-3,3-diphenylalanine cinchonidinium salt (38.2 g) is treated with 950 mL of ethyl acetate and 270 mL of 1N hydrochloric acid solution. The layers are separated and the aqueous phase is extracted with ethyl acetate (3×30 mL). The organic layer is evaporated to afford 19.3 g of a white residue which is used in the next step without further purification. An analytical sample is obtained when a portion of the previous ethyl acetate solution is treated with hexane to precipitate pure product; mp 151°-152° C., $[\alpha]_D^{25} = -60°$ (1% in methanol).

Step C: Preparation of D-(−)-3,3-Diphenylalanine hydrochloride

Crude N-acetyl-D(−)-3,3-diphenylalanine (19.3 g) is treated with 1.5 L of 6N hydrochloric acid solution at reflux for 3 hours. After cooling at room temperature for 4 hours, the mixture is cooled at +2° C. overnight. A white crystalline solid is collected by filtration, washed with diethyl ether (3×50 mL), dried in a vacuum oven at 55° C./200 mm Hg for 15 hours to afford 17.0 g of the title compound; mp 250°-255° C. (dec.), $[\alpha]_D^{25} = -64.5°$ (1% in methanol). Chiral High Pressure Liquid Chromatography (HPLC): Diacel Crownpack CR(−) column. Aqueous HClO$_4$ (perchloric acid), pH 1.5: methanol (84:16), Flow rate =0.5 mL/minute; Ultraviolet (UV) 205 mm. D-Dip—99.6%; L-Dip—0.4%.

Step D: Preparation of D-(−) 3,3-Diphenylalanine

D (−)-3,3-Diphenylalanine hydrochloride (0.5 g) is dissolved in 15 mL of water and the pH of the solution is adjusted with dilute ammonium hydroxide solution to pH 7. The precipitate is collected by filtration, washed with water, boiled with water for a short time, cooled to room temperature, and collected to afford 0.2 g of the title compound; mp 218°-220° C. (dec.).

EXAMPLE 2

L-(+)-3,3-Diphenylalanine

Step A: Preparation of N-Acetyl-L-(+)-3,3-diphenylalanine

Enriched N-acetyl-L(+)-3,3-diphenylalanine cinchonidinium salt (95.9 g) from Example 1 is treated with 1.6 L of ethyl acetate and 400 mL of 1N hydrochloric acid solution. The layers are separated and the aqueous layer is extracted with ethyl acetate (3×50 mL). The ethyl acetate solution is washed with water (3×100 mL), 100 mL of saturated sodium chloride solution, and dried over magnesium sulfate. To the filtered ethyl acetate solution 1 L of hexane is added, and the solution cooled at +2° C. overnight. A precipitate is collected by filtration and dried in a vacuum oven at 55° C./200 mm Hg to afford 11.9 g of N-acetyl-DL-3,3-diphenylalanine; mp171°-173° C.; $[\alpha]_D^{25} = +2°$. The mother liquor is evaporated to afford after drying as above 28 g of the title compound; mp 142°-146° C., $[\alpha]_D^{25} = +47°$ which is used without further purification.

Step B: Preparation of L-(+)-3,3-Diphenylalanine hydrochloride

N-acetyl-L-(+)-3,3-diphenylalanine (28 g) is treated with 2.4 L of 6N hydrochloric acid solution at reflux for 4 hours. The mixture is cooled to room temperature and then at +2° C. overnight. A colored precipitate is collected by filtration, washed with diethyl ether (3×75 mL), and dried at 55° C./200 mm Hg to afford about 30 g of the crude material which is recrystallized from 300 mL of water with charcoaling. After 3 hours at room temperature the first crop of product is collected by filtration. The mother liquor is cooled overnight at +2° C. to afford a second crop. The pink color solids (11.4 g, mp 258°-262° C. (dec.), $[\alpha]_D^{25} = +64.7°$ and 6.38 g, mp 247°-258° C. (dec.), $[\alpha]_D^{25} = +63.8°$, respectively)

are combined and recrystallized from 100 mL of water with charcoaling. After cooling at +2° C. overnight, a precipitate is collected by filtration, washed with diethyl ether (3×50 mL), and dried in a vacuum oven at 55° C./200 mm Hg overnight. This affords the title compound as an off-white crystalline solid; mp 259°–264° C. (dec), $[\alpha]_D^{25} = +63.9°$ (1% in methanol). Chiral HPLC using the procedure of Example 1 L-Dip—99%; D-Dip—1.0%

Step C: Preparation of L-(+)-3,3-Diphenylalanine

Using the methodology of Example 1 (Step D) the title compound is prepared from L-(+)-3,3-diphenylalanine hydrochloride.

EXAMPLE 3

(2R)-3,3-Diphenylalanine hydrochloride

Step A: Preparation of 3,3-Diphenylpropionyl chloride

To a mixture of 3,3-diphenylpropionic acid (20 g, 88.4 mmol) and thionyl chloride (7.74 mL, 106.1 mmol) is added 5 drops of pyridine. The mixture is stirred at room temperature overnight (15 hours), and then distilled in vacuo to afford a light yellow oil, 17.88 g. The title compound forms as a light yellow solid when the oil is refrigerated overnight; mp 41°–43° C.

Step B: Preparation of 2,4,6-Triisopropylbenzenesulfonyl azide

To a stirred solution of 2,4,6-triisopropylbenzenesulfonyl chloride (5.0 g, 16.5 mmol, Aldrich, 97%) in reagent grade acetone (20 mL), initially at 17° C., is added a solution of sodium azide (1.18 g, 18.2 mmol) in water (5 mL) and ethanol (5 mL). The mixture is warmed to 27° C. during the addition. After 2 hours, the reaction is partitioned between dichloromethane and brine. The aqueous solution is extracted with dichloromethane (3×). The combined organic extracts are dried (magnesium sulfate) and concentrated in vacuo. The colorless oil is purified by flash chromatography (silica gel, hexane-dichloromethane, 4:1) to afford the title compound as a white solid, 4.93 g; mp 44°–44.5° C. (Evans, D. A., et. al., *Journal of the American Chemical Society* 112:4011–4030 (1990); mp 43°–44° C.).

Step C: Preparation of (4R,5S) 4-Methyl-5-phenyl-2-oxazolidinone

A round bottom flask, equipped with a distillation apparatus, is charged with (1S,2R)-norephedrine (18.16 g, 99.1 mmol), diethyl carbonate (27.6 mL, 228 mmol), and potassium carbonate (28.9 g, 209 mmol), and heated at 160° C. (oil bath temperature). The distillation head temperature remained at ca 80° C. when ethanol is collected in the collection flask, which is cooled in an ice bath. When the head temperature drops to 60° C. (ca 5 hours), the oil bath is removed and the mixture is cooled to room temperature. The mixture is diluted in dichloromethane and washed with water (2×) and dried (magnesium sulfate). Concentration in vacuo affords an off-white solid (17.88 g), which is recrystallized in hexane-ethyl acetate 1:1.5, to afford the title compound as white crystals, 15.2 g; mp 120–121° C., $[\alpha]_D = 171.4°$ (2.042% in chloroform).

Step D: Preparation of (4R,5S)-3-(1-Oxo-3,3-diphenylpropyl)-4-methyl-5-phenyl-2oxaxolidinone To a solution of (4R,5S)-4-methyl-5 phenyl-2-oxazolidinone (10.63 g, 60.0 mmol) in dry tetrahydrofuran (150 mL), at −78° C., under argon, is added n-butyllithium (39.4 mL, 63 mmol, 1.6 M solution in tetrahydrofuran, Aldrich) dropwise. After the mixture is stirred at −78° C. for 10 minutes, a solution of 3,3-diphenylpropionyl chloride (15.42 g, 63.0 mmol) in tetrahydrofuran is added in one portion. The solution is stirred at −78° C. for 30 minutes and warmed to ambient temperature in 30 minutes. The reaction is quenched with ammonium chloride (saturated aqueous solution). The bulk of tetrahydrofuran is removed in vacuo. The residue is diluted with dichloromethane, washed with sodium hydroxide (1 M), brine, and dried (magnesium sulfate). The concentrated yellow solid is recrystallized in hexane-ethyl acetate (4:1) to afford the title compound as a white solid, 18.5 g; mp 106° C., $[\alpha]_D^{23} = -13.4°$ (1.0% in methanol).

Step E: Preparation of (3(2R),4R,5S)-3-(2-Azido-3,3-diphenyl-1-oxopropyl)-4-methyl -5-phenyl-2-oxaxolidinone To a stirred solution of (4R,5S)-3-(1-oxo-3,3-diphenylpropyl)-4-methyl-5-phenyl -2-oxazolidinone (3.5 g, 9.08 mmol) in dry tetrahydrofuran (150 mL), at −78° C. under argon, is added potassium bis(trimethylsilyl)amide (19.1 mL, 9.53 mmol, 0.5 M solution in toluene, Aldrich). The solution is stirred at −78° C. for 30 minutes, and the solution of 2,4,6-triisopropylbenzenesulfonyl azide (3.5 g, 11.35 mmol) in dry tetrahydrofuran (5 mL) is added. The mixture is stirred for 2 minutes at −78° C. and then quenched by rapid addition of acetic acid (2.4 mL, 41.7 mmol) with immediate warming to 30° C. with a water bath. After stirring at ambient temperature for 2 hours, the mixture is diluted with dichloromethane (400 mL), washed with brine, saturated sodium bicarbonate, and dried (magnesium sulfate). The concentrated yellow oil is purified by flash chromatography (silica gel, hexane-ethyl acetate 5:1) to afford the title compound as a white solid, 2.53 g; mp 89°–91° C., $[\alpha]_D^{23} = -196.3°$ (1.02% in methanol).

Step F: Preparation of (2R)-Azido-3,3 diphenylpropionic acid

To the solution of (3(2R),4R,5S)-3-(2-azido-3,3-diphenyl-1-oxopropyl)-4-methyl-5-phenyl-2-oxazolidinone (2.1 g, 4.92 mmol) in 4:1 tetrahydrofuran-water (50 mL), at 0° C., is added a solution of lithium hydroxide hydrate (0.41 g, 9.84 mmol) in hydrogen peroxide (30%, 2.2 mL, 19.7 mmol), under nitrogen. The milky mixture is stirred at 0° C. for 1 hour. Aqueous sodium sulfite (1M, 10 mL), is added. The bulk of the tetrahydrofuran is evaporated in vacuo. The aqueous solution is cooled in an ice bath and acidified with hydrochloric acid (6N) to pH 1. The white solid is extracted with dichloromethane (5×) and dried (magnesium sulfate). The concentrated oil is purified by flash chromatography (silica gel, hexane-ethyl acetate-acetic acid 50:50:2) to afford the title compound as a white solid, 1.25 g; mp 108°–109.5° C., $[\alpha]_D^{23} = -54.2°$ (1.02% in MeOH). The chiral auxiliary of Step C is recovered as white solid (0.8 g); mp 119°–120° C.

Step G: Preparation of (2R)-3,3-Diphenylalanine hydrochloride (2R)-Azido-3,3-diphenylpropionic acid (0.72 g, 2.69 mmol) and palladium on carbon (0.2 g, 20%) in acetic acid (50 mL) are stirred under 50 pounds per square inch (psi) of hydrogen at 25° C., for 18 hours. The solid is filtered and acetic acid is removed by azeotropic evaporation with heptane. The resulting yellow oil is treated with hydrochloric acid (6N). The solid that forms is recrystallized in hydrochloric acid (6N), decolorized with activated charcoal, to afford the title compound as an off-white solid, 0 57 g; mp 248°–253° C. (dec.), $[\alpha]_D^{23} = -63.7°$ (1.0% in methanol).

In a process analogous to Example 3 the following compound is prepared:

EXAMPLE 4

(2S)-3,3-Diphenylalanine hydrochloride; mp 247°–250° C. (dec), $[\alpha]_D = +63.8°$ (1.0% in methanol;.

EXAMPLE 5

N-(2-Adamantyloxycarbonyl)-D-3,3-diphenylalanine

Step A: Preparation of 2-Adamantyl chloroformate

Triphosgene (0.7 g, 2.4 mmol) is added to 1.0 g (6.6 mmol) of 2-adamantol in 10 mL of ethyl acetate at −3° C. under a nitrogen atmosphere. A solution of 0.53 mL of pyridine in 0.8 mL of ethyl acetate is added through a syringe keeping the temperature at 0° to 5° C. The reaction mixture is stirred a 0° C. for 15 minutes and then at room temperature for 1 hour. The salts are filtered and the clear solution is used in the next step without further purification or the ethyl acetate is removed in vacuo and the residue redissolved in an appropriate solvent.

Step B: Preparation of N-(2-Adamantyloxycarbonyl)-D(−)-3,3-diphenylalanine

D-(−)-3,3-Diphenylalanine hydrochloride (Example 1, Step C) (0.1 g, 0.36 mmol) is dissolved in 1.5 mL of 1N-sodium hydroxide solution and 1 mL of tetrahydrofuran and the solution cooled to 0° C. A solution of 0.075 g (0.36 mmol) of 2-adamantyl chloroformate in 1 mL of tetrahydrofuran is added dropwise and the mixture stirred at 0° C. for 15 minutes and then at room temperature for 1 hour. The reaction mixture is acidified with 6N hydrochloric acid solution to pH 1 and extracted with dichloromethane. The organic layer is washed with water, dried with magnesium sulfate, and the solvent evaporated in vacuo to afford 0.14 g of crude product. The crude product is dissolved in 2.5 mL of boiling ethanol, mixed with water to cloudiness, and extracted with dichloromethane as described above. Evaporation of the dried organic solution (magnesium sulfate) affords 0.11 g of the title compound as a glassy solid; Rf=0.65 (silica gel, hexane:ethanol 1:3); $[\alpha]_D^{25} = 14.9°$ (1% in methanol).

In a process analogous to Example 5 the following compound is prepared:

EXAMPLE 6

N-(2-Adamantyloxycarbonyl)-L-3,3-diphenylalanine

EXAMPLE 7

N-Benzyloxycarbonyl-D-3,3-diphenylalanine

D-(−)-3,3-Diphenylalanine hydrochloride (Example 1, Step C) (0.1 g, 3.6 mmol) is dissolved in 5.4 mL of 2N sodium hydroxide solution and cooled to 0° C. Benzyl chloroformate (0.6 mL) and 2.1 mL of 2N sodium hydroxide solution are added alternatively, keeping the pH above 8 and the temperature at <10° C. After addition is complete, the ice bath is removed and the reaction mixture is stirred at room temperature for 30 minutes. Ethyl acetate (20 mL) is added and the aqueous phase is further extracted with ethyl acetate (3×5 mL). The combined organic extracts are dried (magnesium sulfate), filtered, and the solvent evaporated in vacuo to afford 1.11 g of crude product as a clear oil which contains ethyl acetate. After drying under vacuum at 55° C., the title compound is obtained (0.67 g); mp 80°–90° C. Rf =0.73 (silica gel, hexane-ethyl acetate 1:3).

In a process analogous to Example 7 the following compound is prepared:

EXAMPLE 8

N-Benzyloxycarbonyl-L 3,3-diphenylalanine

EXAMPLE 9

Ac-D-Dip-Leu-Asp-Ile-Ile-Tro

The linear hexapeptide is prepared by standard 0 solid phase synthetic peptide methodology utilizing a Boc/benzyl strategy (Stewart, J. M. and Young, J. D., *Solid Phase Peptide Synthesis*, Pierce Chemical Co., Rockford, IL, 1984). Protected amino acids and reagents are obtained from commercial sources with the exception of N-α-Boc D Dip and are not further purified. The protected peptide resin is prepared on an Applied Biosystems 430A Peptide Synthesizer, utilizing protocols supplied for a dicyclohexylcarbodiimide mediated coupling scheme (Standard 1.0, Version 1.40). Starting with 0.560 g of N-α-Boc-Trp(For)-PAM resin (0.88 meq/g, 0.43 meq of Boc-Trp(For) total) the protected peptide is prepared by the stepwise coupling of the following amino acids (in order of addition): N-α-Boc-D-Dip, N-α-Boc-Leu.H₂O, N-α-Boc-Asp(Bzl), and N-α-Boc-Ile.0.5 H₂O. A typical cycle for the coupling of an individual amino acid residue is illustrated below (reproduced from the ABI manual):

All the single couple RV cycles conform to the following pattern:
(1) 33% TFA in DCM for 80 seconds
(2) 50% TFA in DCM for 18.5 minutes
(3) Three DCM washes
(4) 10% DIEA in DMF for 1 minute
(5) 10% DIEA in DMF for 1 minute
(6) Five DMF washes
(7) Coupling period
(8) Five DCM washes After the coupling of N-α-Boc-D-Dip, the Boc group is removed with the end-NH₂ cycle and the free amine is acetylated with N-acetylimidazole (1.0 g, 120 minutes) in 20 mL of dichloromethane (DCM). The resin is washed with DCM (3×20 mL) and dried under reduced pressure (0.878 g).

The peptide is liberated from the solid support and the carboxylate of aspartic acid deprotected by treatment with anhydrous hydrogen fluoride (9.0 mL), anisole (1.0 mL), and dimethyl sulfide (0.5 mL) (60 minutes, 0° C.). After removing the hydrogen fluoride under a stream of nitrogen, the resin is washed with diethyl ether (3×30 mL) and extracted with 20% HOAc in water (3×30 mL) and glacial HOAc (2×30 mL). The aqueous extractions are combined, concentrated under reduced pressure, and lyophilized (320 mg). To remove the formyl protecting group, the crude peptide is suspended in 50 mL of aqueous 0.1 N KOH at 0° C. for 2 minutes. The pH of the solution is adjusted to less than 4.0 with 10% HCl/H₂O and passed through a C 18 (60 cc) cartridge. The cartridge is washed with H₂ O (50 mL), eluted with 0.1% TFA, 70% CH$_3$CN in H$_2$O, the eluants combined, concentrated under reduced pressure (10 mL), diluted with H$_2$O, and lyophilized to yield 153 mg of a white powder. The crude peptide is dissolved in 4.0 mL of 50% TFA/H$_2$O, filtered through a 0.4 μM syringe filter, and chromatographed on a Vydac 218TP 1022 column (2.2×25.0 cm, 15.0 mL/min, A:0.1% TFA/H$_2$O, B:0.1% TFA/CH$_3$CH, Gradient; 0% B for 10 minutes, 10% to 50% B over 120 minutes). Individual fractions are collected and combined based upon analysis by analytical HPLC. The combined fractions are concentrated under reduced pressure (10 mL), diluted with H$_2$O (50 mL), and lyophilized (14.8 mg). The homogeneity and structure of the resulting peptide is confirmed by analytical HPLC, capillary zone electrophoresis, Proton Nuclear Magnetic Resonance Spectroscopy (H$^1$-NMR) and Fast Atom Bombardment Mass Spectroscopy (FAB-MAS), MNa+946.6.

PREPARATION OF STARTING MATERIALS

EXAMPLE A

DL-3,3-Diphenylalanine hydrochloride

Step A: Preparation of Ethyl N-diphenylmethyleneglycinate

Benzophenone imine (100 g, 0.54 mol), and 78.4 g, 0.56 mol) ethyl glycinate hydrochloride are combined in 2 L of dichloromethane and stirred overnight at room temperature. A precipitate (ammonium chloride) is filtered and the solution washed with water, dried over magnesium sulfate, and concentrated. The residual oil is dissolved in 200 mL of boiling diethyl ether, cooled to room temperature, and diluted with 600 mL of hexane. Some seed crystals from a previous experiment are added and the mixture cooled at +2° C. overnight. A white crystalline precipitate is collected and the mother liquor is concentrated to one-half of the volume, cooled overnight as above. This affords a second crop of product. The total yield is 133.0 g of the title compound; mp 52°-54° C.

Step B: Preparation of Ethyl N-(diphenylmethylene)-DL-3,3-diphenylalanine

Ethyl N-diphenylmethyleneglycinate (121.5 g, 0.45 mol) is dissolved in 1.5 L of dichloromethane and added to a solution of diphenylmethyl bromide (140 g) in 0.5 L of dichloromethane. Tetrabutylammonium bromide (75 g, 0.23 mol) and a 50% aqueous solution of sodium hydroxide (475 mL) are added, and the mixture stirred at room temperature for 3 hours. Then 0.6 L of dichloromethane and 0.6 L of water are added to the previous reaction mixture. The layers are separated and the organic phase washed with water (3×), dried over magnesium sulfate, and concentrated to give a lemon-yellow product which is used as is in the next step.

Step C: Preparation of DL-3,3-Diphenylalanine hydrochloride

Crude ethyl N-(diphenylmethylene)-DL 3,3-diphenylalaninate is added to 2.5 L of 6N hydrochloric acid solution and heated at reflux for 6 hours. The reaction mixture is allowed to cool to room temperature overnight. The product is collected, washed with water (3×), diethyl ether (4×), and dried at 50° C./200 mm Hg. This affords 93.6 g of the title compound as a white crystalline material; mp >210° C. (dec).

EXAMPLE B

N-Acetyl-DL-3,3-diphenylalanine

DL-Diphenylalanine hydrochloride (93.5 g, 0.337 mol) (Example A) is dissolved in 935 mL of 1N sodium hydroxide solution, warmed and filtered to remove insolubles. A 2 L flask equipped with a mechanical stirrer, two dropping funnels, and an electrode to monitor pH is charged with the previous clear solution. The reaction mixture is cooled in an ice bath and acetic anhydride (35 mL, 0.37 mol) and 1N sodium hydroxide (175 mL) are added dropwise at a rate to keep pH ≧10. After the acetic anhydride is added (ca 30 minutes) more sodium hydroxide solution is added to stabilize the mixture at pH 10. Then the solution is stirred for an additional 2 hours.

The reaction mixture is acidified to pH 1 with concentrated hydrochloric acid to yield a white precipitate which is filtered and dissolved in 1.25 L of warm ethyl acetate. The organic layer is washed with 50 mL of water and 50 mL of saturated sodium chloride solution, and dried over magnesium sulfate. Hexane (750 mL) is added to the filtered ethyl acetate solution and the solution is cooled at +2° C. for 15 hours. A white precipitate is collected by filtration, dried at 55° C./200 mm Hg overnight, affording 68.8 g of the title compound; mp 171°-173° C. Additional hexane (500 mL) is added to the mother liquor and after cooling for 15 hours a second crop is collected and dried as above to give an additional 10.65 g of the title compound; mp 170°-171° C.

We claim:

1. A process for the preparation of the D(−) and L(+) enantiomers of a compound of Formula I

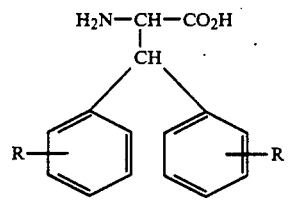

and pharmaceutically acceptable salts thereof wherein R is hydrogen, chloro, bromo, fluoro, methyl, trifluoromethyl, methoxy, 2,4-dichloro, or 2,4-difluoro which comprises:

step (a) treating a racemic compound of Formula II

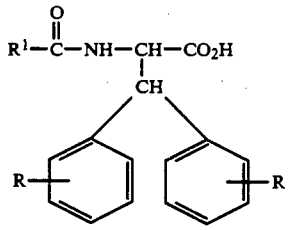

wherein
R$^1$ is a lower alkyl,
CX$_3$ wherein X is hydrogen or halogen or aryl and R is as defined above;
wherein (−) cinchonidine is a solvent selected from the group consisting of methanol, ethanol, propanol, and butanol to afford a racemic compound of Formula III;

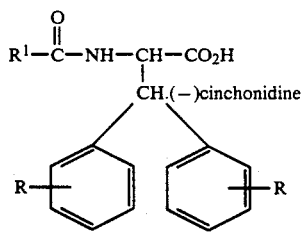

wherein R and R¹ are as defined above;

Step (b) resolving a compound of Formula III wherein R and R¹ are as defined above by fractional crystallization into D(−) and L(+) enantiomers;

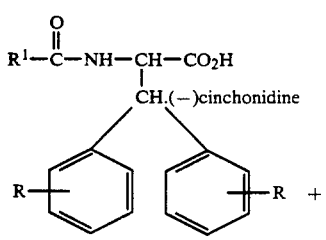

+

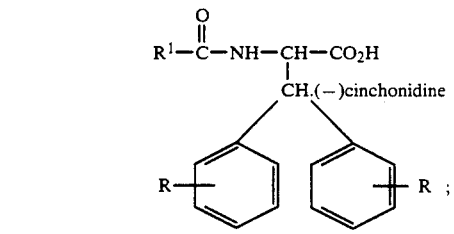

Step (c) treating a compound of Formula D(−)IIIa or Formula L(+)IIIb wherein R and R¹ are as defined above with an acid in a solvent selected from the group consisting of ethyl acetate, dichloromethane, chloroform, toluene, tetrahydrofuran and diethyl ether to afford a compound of Formula D(−)IIa or Formula L(+)IIb:

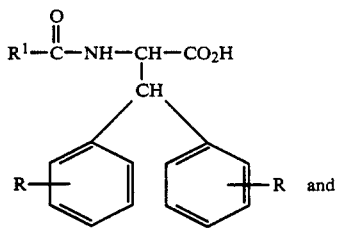

and

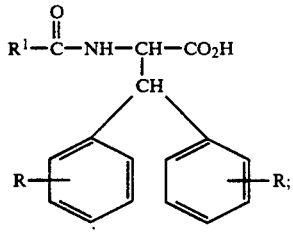

Step (d) heating a compound of Formula D(−) IIa or Formula L(+)IIb wherein R and R¹ are as defined above with an acid to afford the D(−)Ia or L(+)Ib enantiomers of Formula I;

Step (e) and, if desired, converting a compound of Formula D(−)Ia or Formula L(+)Ib to a corresponding pharmaceutically acceptable salt and if so desired, converting the corresponding pharmaceutically acceptable salt to a compound of Formula D(−)Ia or Formula L(+)Ib.

2. A process according to claim 1 wherein the solvent in Step (a) is methanol.

3. A process according to claim 1 wherein the solvent in Step (c) is ethyl acetate.

4. A process according to claim 1 wherein the acid in Step (c) is hydrochloric acid.

5. A process according to claim 1 wherein the acid in Step (d) is hydrochloric acid.

6. A process according to claim 1 wherein the compound of Formula D(−)IIa or Formula L(+)IIb is refluxed in 6N hydrochloric acid solution.

7. A process according to claim 1 for the preparation of D-(−)-3,3-diphenylalanine and L-(+)-3,3-diphenylalanine and pharmaceutically acceptable salts thereof.

8. A compound selected from the group consisting of

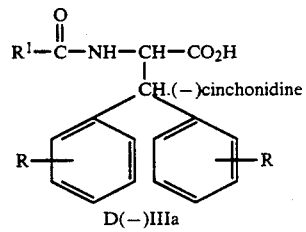

and

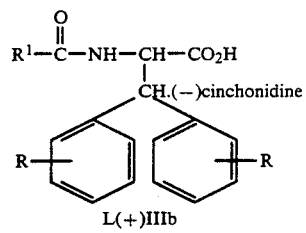

wherein 'R is
  hydrogen
  chloro,
  bromo,
  fluoro,
  methyl,
  trifluoromethyl,
  methoxy,
  2,4-dichloro, or
  2,4-difluoro and
R¹ is lower alkyl,
  CX₃ wherein X is hydrogen or halogen or aryl.

9. A compound selected from the group consisting of

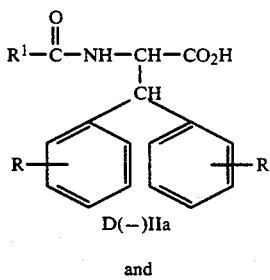

D(−)IIa and

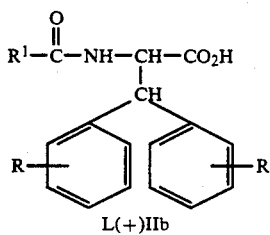

L(+)IIb wherein
R is hydrogen chloro, bromo, fluoro, methyl, trifluoromethyl, methoxy, 2,4-dichloro, or 2,4-difluoro and
$R^1$ is lower alkyl,
$CX_3$ wherein X is hydrogen or halogen or aryl and pharmaceutically acceptable salts thereof.

10. A compound selected from the group consisting of

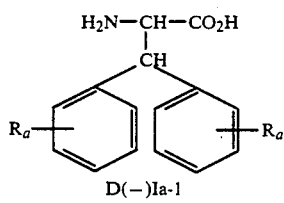

D(−)Ia-1 and

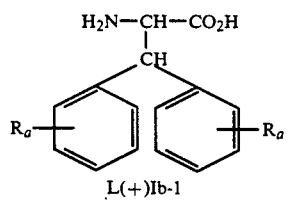

L(+)Ib-1 wherein
$R_a$ is chloro, bromo, fluoro, methyl, trifluoromethyl, methoxy, 2,4-dichloro, or 2,4-difluoro
and pharmaceutically acceptable salts thereof.

11. A compound selected from the group consisting of

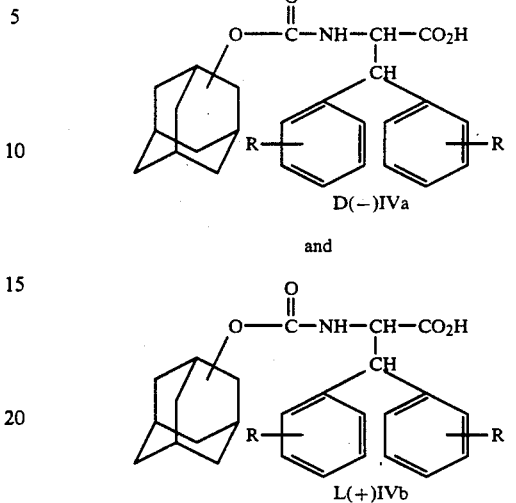

D(−)IVa and

L(+)IVb wherein
R is hydrogen, chloro, bromo, fluoro, methyl, trifluoromethyl, methoxy, 2,4-dichloro, or 2,4-difluoro
and pharmaceutically acceptable salts thereof.

12. A compound selected from the group consisting of

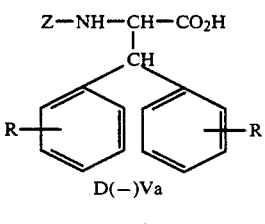

D(−)Va and

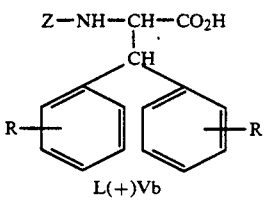

L(+)Vb wherein
Z is benzyloxycarbonyl,
R is hydrogen chloro, bromo, fluoro, methyl, trifluoromethyl, methoxy, 2,4-dichloro, or 2,4-difluoro, and
pharmaceutically acceptable salts thereof.

* * * * *